United States Patent [19]

Kjellin et al.

[11] 4,338,319

[45] Jul. 6, 1982

[54] METHOD FOR THE TREATMENT OF CHRONIC OBSTRUCTIVE AIRWAY OR CARDIAC DISEASES

[75] Inventors: Per G. Kjellin, Lund; Carl G. A. Persson, Löberöd, both of Sweden

[73] Assignee: Aktiebolaget Draco, Lund, Sweden

[21] Appl. No.: 209,007

[22] Filed: Nov. 21, 1980

[30] Foreign Application Priority Data

Nov. 27, 1979 [SE] Sweden ............................. 7909780

[51] Int. Cl.$^3$ ............................................. A61K 31/52
[52] U.S. Cl. .................................................... 424/253
[58] Field of Search ........................................ 424/253

[56] References Cited

U.S. PATENT DOCUMENTS 2,767,182 10/1956 Konz et al. ................... 260/255

FOREIGN PATENT DOCUMENTS 49-004469 2/1974 Japan .
52-139093 of 1977 Japan .
683523 12/1952 United Kingdom .

OTHER PUBLICATIONS

LeRoy et al., J. Pharm. Exptl. Ther. 69 (1940) pp. 45–51.
Ruttink, Rec. Trav. Chim., 57 (1938) 819–823 (C.A. 32:9292$^6$, 1938).
Ruttink, Chem. Abstr. 32:7476$^2$, 1938.
Rec. Trav. Chim. 65 (1946) pp. 751–767.
Ohtsuka, Bull. Chem. Soc. Jap. 1973 (46) 2, p. 507.
Chemische En Pharmakologische Onderzoekingen in de Purinereeks, in het Bijzonder von Aethyl-xanthinen, Diss. Delft, 1938.

Primary Examiner—Frank Cacciapaglia, Jr.
Attorney, Agent, or Firm—Brumbaugh, Graves, Donohue & Raymond

[57] ABSTRACT

A method for the treatment of chronic obstructive airway disease or cardiac disease by administration 3-ethylxantine or a pharmaceutically acceptable salt thereof; a pharmaceutical preparation containing 3-ethylxanthine.

3 Claims, No Drawings

METHOD FOR THE TREATMENT OF CHRONIC OBSTRUCTIVE AIRWAY OR CARDIAC DISEASES

TECHNICAL FIELD

The present invention is related to a novel method of treating chronic obstructive airway disease (COAD) or cardiac disease by administration of 3-ethylxanthine as well as to pharmaceutical preparations containing 3-ethylxanthine.

The object of the present invention is to provide a method for treatment of COAD and cardiac disease without producing untoward side-effects as emesis and convulsions.

A further object of this invention is to provide a pharmaceutical preparation to be used in the treatment of COAD and cardiac disease.

BACKGROUND ART 3-ethylxanthine has been studied regarding its vasodilatory effects (LeRoy et al.; J. Pharm. Exptl. Ther. 69 (1940) pages 45–51). Furthermore, J. Ruttink (Rec. trav.chim. 57 (1938) 819–823 and Chemische En Pharmakologische Onderzoekingen in de Purinereeks, in het Bijzonder van Aethyl-xanthinen, Diss. Delft, 1938) has studied the effect of 3-ethylxanthine on frog muscle, its diuretic effect and its effect on the heart and the central nervous system.

Theophylline and various salts thereof are used in the treatment of chronic obstructive airway disease (COAD) and cardiac disease. Major therapeutic effects of theophylline are to relax bronchial smooth muscle and stimulate heart muscle. The major drawback with theophylline therapy is that the drug with a significant frequency produces toxic side-effects; most common are nausea and gastric distress, most serious are convulsions, which may lead to death.

DISCLOSURE OF THE INVENTION

It has been found according to the present invention that 3-ethylxanthine

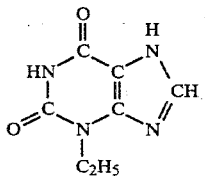

or a pharmaceutically acceptable salt thereof possesses certain pharmacologically advantages not previously observed. This advantageous property makes 3-ethylxanthine valuable in the treatment of chronic obstructive airway disease (COAD) and of cardiac disease, such as congestive heart failure.

Theophylline is extensively used in the treatment of COAD and cardiac disease.

The most common and dose limiting side effects of the bronchodilator and cardiotonic drug theophylline (1,3-dimethylxanthine) are nausea and vomiting.

3-ethylxanthine is about equally potent to theophylline as a bronchodilator and cardiac stimulant. Surprisingly, no emetic or other toxic effect of 3-ethylxanthine were found when given in doses up to 2–2.5 times those where theophylline produced vomiting or convulsions and death.

Theophylline exhibits marked variations between patients in its plasma clearance rate because it is metabolized at such varying rates. Therapy with theophylline is much complicated by this fact. Therefore, a further important advantage over theophylline with 3-ethylxanthine is the finding that it is not metabolized. 100% of the given amount of the drug is recovered in the urine as unchanged 3-ethylxanthine. This indicates that treatment with 3-ethylxanthine should lead to predictable serum concentrations with negligible interindividual variations.

Methods for the preparation of 3-ethylxanthine can be found in Japanese Pat. No. 74004469 and in Rec. trav.chim. 65 (1946) 751–767.

This invention also takes into consideration that a compound which structurally deviates from 3-ethylxanthine after administration to a living organism may be transformed therein to 3-ethylxanthine and in this form exert its effect. This consideration is a further aspect of this invention.

The present invention includes pharmaceutically acceptable salts of the compound of formula (I) with pharmaceutically acceptable bases. By the term "pharmaceutically acceptable salts" is meant salts the cations of which are relatively innocuous to the animal organism when used in therapeutic doses so that the beneficial pharmacological properties of the parent compound of general formula (I) are not vitiated by side effects ascribable to those cations. Suitable salts include the alkali metal, e.g. sodium and potassium and ammonium salts and salts of amines known in the art to be pharmaceutically acceptable, e.g. glycine, ethylene diamine, choline, diethanolamine, triethanolamine, octadecylamine, diethylamine, triethylamine, 1-amino-2-propanol, 2-amino-2-(hydroxymethyl)propane-1,3-diol and 1-(3,4-dihydroxyphenyl)-2-isopropylaminoethanol.

Pharmaceutically acceptable salts may be prepared by the reaction together of stoichiometric quantities of a compound of formula (I) and the appropriate base, that is to say, a base as described immediately hereinbefore, for example at an elevated temperature, with or without an appropriate solvent, preferably followed by recrystallisation from an appropriate solvent, for example a hydroxylic solvent, e.g. water, of the salt so formed.

In clinical practice the compound of the present invention will normally be administered orally, rectally, nasally, sublingually, by injection or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention.

Usually the active substance will comprise between 0.1 and 99% by weight of the preparation, for example 0.5 and 20% for preparations intended for injection and between 0.1 and 50% for preparations intended for oral administration.

To produce pharmaceutical preparations in the form of dosage units for oral application containing the compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative, polyvinylpyrrolidone or gelatine and also may include lubricants such as magnesium or calcium stearate or a Carbowax ® or other polyethylene glycol waxes and compressed to form tablets or cores for dragées. If dragees are required, the cores may be coated, for example with concentrated sugar solutions which may contain gum arabic, talc and/or titanium dioxide, or alternatively with a film forming agent dissolved in easily volatile organic solvents or other suitable solvent or mixtures or organic solvents. Dyestuffs can be added to these coating for example, to distinguish between different contents of active substance. For the preparation of soft gelatin capsules (pearl-shaped closed capsules) consisting of gelatine and, for example, glycerol as a plasticizer, or similar closed capsules, the active substance may be admixed with a Carbowax ® or a suitable oil as e.g. sesam oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives, polyvinylpyrrolidone or gelatine, and may also include magnesium stearate or stearic acid as lubricants.

The compound of the invention may also be formulated as a sustained action dosage form using suitable excipients. Different methods may be used for the availability control e.g. diffusion process and ion exchange. Methods using the diffusion process may be exemplified by products involving coated granules or particles, matrix imbedded drug and slightly soluble forms.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbic acid, and citric acid, and for example aroma.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally aroma, saccharine and/or carboxymethylcellulose as a dispersing agent.

For parenteral application by injection preparations may comprise an aqueous solution or suspension of the active substance according to the invention, desirably in a concentration of 0.5–10%, and optionally also a stabilizing agent and/or buffer substances in aqueous solution. Dosage units of the solution may advantageously be enclosed in ampules.

The dosage at which the active ingredient is administered may vary within a wide range and will depend on various factors such as for example the individual requirements of each patient. A suitable oral dosage range is from 100 to 2000 mg given 1–4 times a day. A suitable dosage range at parenteral administration is from 20 to 500 mg.

The pharmaceutical compositions containing the active ingredient may suitably be formulated so that they provide doses within these ranges either as single dosage units or as multiple dosage units.

WORKING EXAMPLES

EXAMPLE 1

Preparation of 3,7-dihydro-3-ethyl-1H-purine-2,6-dione VI (3-ethylxanthine)

a. Preparation of 6-amino-1-ethyl-2,4-(1H,3H)-pyrimidinedione II

To a solution of 127.5 g (1.5 mol) cyanoacetic acid and 200 ml of acetic anhydride was added 120 g (1.36 mol) of ethylurea. The solution was stirred at 60°–70° C. for 2 hours. After cooling, white crystals were filtered off and washed with ethanol. Yield 153 g (74%) (I). This was stirred in 1 liter of hot water and 160 ml of 2 N NaOH was added in portions so the solution the whole time was basic. The reaction mixture was refluxed for 20 minutes and then neutralized with 5 N HCl. After cooling, white crystals were filtered off. Yield 100 g (65%) (II) NMR.

b. Preparation of 6-amino-1-ethyl-5-nitroso-2,4-(1H,3H)-pyrimidinedione III

To 100 g (0.65 mol) of 6-amino-1-ethyl-2,4-(1H,3H)-pyrimidinedione (II), dissolved in 1 liter hot water, was added 145 ml of 5 N HCl and 50 g of $NaNO_2$ (0.72 mol) which was dissolved in water. After cooling the red crystals were filtered off and washed with water. Yield 97.7 g (83%) (III) NMR.

c. Preparation of 5,6-diamino-1-ethyl-2,4-(1H,3H)-pyrimidinedione IV

To a suspension of 97 g of 6-amino-1-ethyl-5-nitroso-2,4-(1H,3H)-pyrimidinedione (III) was added 240 g of sodium dithionit in portions. The pale red crystals were filtered off and washed with water. Yield 89 g (99%) IV. NMR ($DMSOd_6$, 2.60), 1.13 (t,3H), 3.30 (s broad, 2H), 3.93 (q,2H), 6.23 (s,2H), 10.00 (s broad, 1H).

d. Preparation of 3,7-dihydro-3-ethyl-1H-purine-2,6-dione VI

A solution of 89 g of 5,6-diamino-1-ethyl-2,4-(1H,3H)-pyrimidinedione (IV) in 200 ml of formic acid was refluxed for 2 hours. The hot solution was added to 1 liter of acetone. The received crystals were filtered off.

The amide (V) was refluxed in 300 ml of 2 N NaOH for 1 hour and then neutralized with 5 N HCl. The crystals were filtered off and recrystallized from 700 ml of acetic acid. Yield 52.2 g (55%) (VI) NMR.

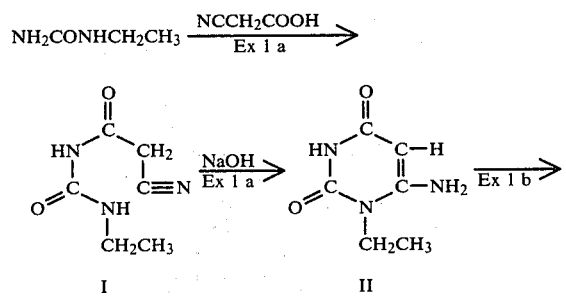

-continued

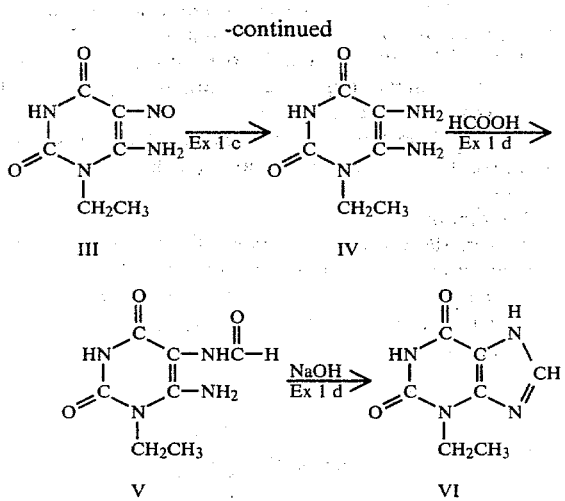

The following Examples illustrate how the compounds of the invention can be incorporated in pharmaceutical compositions.

| Example 2. Aerosol for inhalation | |
|---|---|
| Active substance | 1.50 g |
| "Miglyol" (Registered Trade Mark) | 0.20 g |
| "Frigen" (Registered Trade Mark) 11/12/113/114 | ad 100.0 g |

"Frigen" is used to denote the halogenated hydrocarbons. "Frigen" 114 is 1,2-dichloro-1,1,2,2-tetrafluorethane, "Frigen" 113 is 1,1-difluoro-2,2-dichlorotrifluorotrichloroethane, "Frigen" 11 is trichloromonofluoromethane and "Frigen" 12 is dichlorodifluoromethane. "Miglyol" denotes a triglyceride of saturated vegetable oils. Or a pulver aerosol where the active substance is mixed with lactose.

| Example 3. Tablets | |
|---|---|
| Each tablet contains | |
| Active substance | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 350.0 mg |
| Example 4. Suppositories | |
| Each suppository contains | |
| Active substance | 50.0 mg |
| Ascorbyl palmitate | 1.0 mg |
| Suppository base (Imhausen H) | ad 2000.0 mg |
| Example 5. Injection solution | |
| Active substance | 2.000 mg |
| Sodium hydroxide | 0.310 mg |
| Sodium purosulphite | 0.500 mg |
| Disodium edetate | 0.100 mg |
| Sodium chloride | 8.500 mg |
| Sterile water for injection | ad 1.00 g |
| Example 6. Sublingual tablets | |
| Each tablet contains | |
| Active substance | 20.0 mg |
| Lactose | 85.0 mg |
| Agar | 5.0 mg |
| Talc | 5.0 mg |

Pharmacological Tests

Isolated Guinea-Pig Hearts

From the bled guinea-pigs, the hearts were immediately removed and perfused (in retrograde direction through the cannulated aorta) with oxygenated Krebs solution at 37° according to Langendorff. The heart was mounted in a thermostatically controlled organ bath (50 ml) containing Krebs solution. A saline-filled, open-end polyethylene catheter was inserted into the right ventricle through the pulmonary artery. The catheter was fixed to the pulmonary artery by a ligature just above the valvular plane. It was connected to a pressure transducer (P23 AC), making it possible to record changes in intraventricular pressure. From these, the contraction frequency was obtained. Drugs were given as single bolus injections into the perfusion solution.

Isolated human bronchial muscle

Sections of human lungs were obtained from patients undergoing surgical pneumotomy for lung tumour. Airways of various sizes were carefully dissected and mounted in an organ bath containing well aerated (95% $O_2$+5% $CO_2$) Kreb's solution at 37° C. Isometric tension changes were recorded by means of a force displacement transducer (Grass FT03) and a Grass polygraph. Basal tension level was set up at 0.5-1 g. The relaxing effects (cumulative dose-response) of theophylline and 3-ethylxanthine were evaluated on each airway preparation contracted by carbacholine 0.1 μg/ml.

Emetic and convulsive effects in unanaesthetized cats

Cats of either sex, freshly fed, received the test compound as slow intravenous injection through v. cephalica. After administration the animals, kept isolated, were observed regularly for 6 hours.

Urinary excretion of 3-ethylxanthine

25 μmol of 3-ethylxanthine was injected intravenously in the tail vein (0.2 ml/100 g) of Sprague-Dawley rats. Urine was collected for 24 hours. Urine samples, 10 μl, were diluted ten times with mobile phase and analyzed by means of HPLC. The concentration of unchanged drug was determined by comparing peak heights in the sample and from an injected standard diluted with rat urine. (Column Nucleosid $C_{18}$ 5 μn 200×5 mm mobile phase acetonitrile water 5/95 v/v).

The identity of unchanged substance was confirmed on basis of its retention time.

Results 3-ethylxanthine is about equally potent to theophylline as a bronchodilator and cardiac stimulant, see Table 1.

TABLE 1

Potency ratios between 3-ethylxanthine and theophylline obtained in isolated perfused guinea-pig hearts and in isolated strips of human bronchial muscle.

| | Guinea-pig heart | | Human isolated bronchial muscle relaxant activity |
|---|---|---|---|
| | positive chronotropic activity | positive inotropic activity | |
| Theophylline | 1 | 1 | 1 |
| 3-ethylxanthine | 1 (n = 3) | 1 (n = 3) | 0.9 (n = 9) |

TABLE 2

Emetic and convulsive effects of theophylline and 3-ethylxanthine in conscious cats.

| Compound | Dose mg/kg | No of animals | Vomiting | Convulsion |
|---|---|---|---|---|
| Theophylline | 50 | 3 | 0/3 | 0/3 |
| Na-salt | 55 | 5 | 1/5 | 0/5 |
| | 60 | 6 | 3/6 | 2/6[1] |
| | 66 | 5 | 2/5 | 0/5 |
| | 72 | 7 | 0/7 | 2/7[1] |
| | 77 | 5 | 1/5 | 0/5 |
| | 82 | 3 | 0/3 | 3/3[1] |
| 3-ethyl-xanthine Na-salt | 40 | 2 | 0/2 | 0/2 |
| | 50 | 2 | 0/2 | 0/2 |
| | 60 | 2 | 0/2 | 0/2 |
| | 90 | 2 | 0/2 | 0/2 |
| | 110 | 2 | 0/2 | 0/2 |
| | 130 | 2 | 0/2 | 0/2 |
| | 160 | 2 | 0/2 | 0/2 |

[1]All convulsing cats died rapidly after the injection was completed.

The nauseatic and convulsive effects of theophylline and 3-ethylxanthine were studied after single slow intravenous administration to conscious cats. Theophylline in doses $\geq 55$ mg/kg produced emesis and/or other CNS-effects such as convulsions and acute death. 3-ethylxantine $\leq 160$ mg/kg did not produce emesis convulsions, see Table 2.

TABLE 3

Urinary excretion of 3-ethylxanthine

| Rat. No. | Weight (gram) | Total amount of 3-ethyl-xanthine given (mg) | Total amount of 3-ethyl-xanthine given (mg) | Excreted as unchanged drug (%) |
|---|---|---|---|---|
| 1 | 225 | 1.01 | 0.99 | 98 |
| 2 | 220 | 0.99 | 1.03 | 104 |
| 3 | 236 | 1.06 | 1.14 | 108 |

After i.v. injection 100% of the given dose was recorded in the urine as unchanged drug, see Table 3.

The identity of unchanged substance was confirmed on basis of its retention time.

In conclusion:

1. 3-ethylxanthine was as potent as theophylline as a bronchodilator and cardiac stimulant.

2. 3-ethylxanthine did not produce emetic or convulsive effects indicating a significant pharmacodynamic advantage over theophylline.

3. 3-ethylxanthine was not metabolized indicating a significant pharmacokinetic advantage over theophylline.

We claim:

1. A method for the treatment of chronic obstructive airway disease treatable by theophylline therapy, characterized in administering to a host suffering therefrom a therapeutically active dose of a compound of the formula

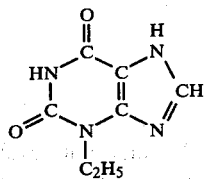

2. A method for the treatment of cardiac disease treatable by theophylline therapy, characterized in administering to a host suffering therefrom a therapeutically active dose of a compound of the formula

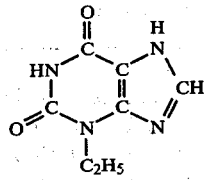

or a pharmaceutically acceptable salt thereof.

3. A method according to claim 1 or 2 comprising oral administration dosages of 100–2000 mg of a compound of the formula I or a pharmaceutically acceptable salt thereof 1–4 times/day.

* * * * *

UNITED STATES PATENT OFFICE
CERTIFICATE OF CORRECTION

Patent No. 4,338,319    Dated July 6, 1982

Inventor(s) Per Gunnar Kjellin et al.

It is certified that error appears in the above-identified patent and that said Letters Patent are hereby corrected as shown below:

Page 1, Col. 2, in the Abstract, line 3, "ethylxantine" should read -- ethylxanthine --;
Col. 1, line 53, "pharmacologically" should read -- pharmacological --;
Col. 3, lines 10-11, "coating" should read -- coatings --;
Col. 7, line 26, "ethylxantine" should read -- ethylxanthine --;
Col. 7, line 26, after "emesis" insert -- or --;
Col. 7, in the heading of Table 3 at the fourth column, "given" should read -- found --;
Col. 8, line 17, following the chemical formula insert -- I --;
Col. 8, line 32, following the chemical formula insert -- I --.

Signed and Sealed this

Nineteenth Day of October 1982

[SEAL]

Attest:

GERALD J. MOSSINGHOFF

Attesting Officer    Commissioner of Patents and Trademarks